United States Patent
Han et al.

(10) Patent No.: US 6,492,186 B1
(45) Date of Patent: Dec. 10, 2002

(54) METHOD FOR DETECTING AN ENDPOINT FOR AN OXYGEN FREE PLASMA PROCESS

(75) Inventors: Qingyan Han, Columbia; Palani Sakthivel; Ricky Ruffin, both of Gaithersburg; Andre Cardoso, Laurel, all of MD (US)

(73) Assignee: Eaton Corporation, Cleveland, OH (US)

( * ) Notice: Subject to any disclaimer, the term of this patent is extended or adjusted under 35 U.S.C. 154(b) by 0 days.

(21) Appl. No.: 09/434,617

(22) Filed: Nov. 5, 1999

Related U.S. Application Data (63) Continuation-in-part of application No. 09/368,553, filed on Aug. 5, 1999, now Pat. No. 6,281,135.

(51) Int. Cl.[7] .............................................. H01L 21/00
(52) U.S. Cl. ............................. 438/8; 438/9; 438/725; 216/60; 156/345
(58) Field of Search ................... 216/60, 68; 156/345; 438/723, 725, 9, 14, 8, 16

(56) References Cited

U.S. PATENT DOCUMENTS

| | | | |
|---|---|---|---|
| 4,201,579 A | 5/1980 | Robinson et al. | 430/323 |
| 4,341,592 A | 7/1982 | Shortes et al. | 430/328 |
| 4,491,499 A | 1/1985 | Jerde et al. | 156/626 |
| 4,695,700 A | 9/1987 | Provence et al. | 219/121 |
| 4,980,022 A * | 12/1990 | Fujimura et al. | 156/643 |
| 5,168,803 A * | 12/1992 | Miyakawa | 437/197 |
| 5,498,308 A | 3/1996 | Kamarehi et al. | 156/345 |
| 5,694,207 A | 12/1997 | Hung et al. | 356/72 |
| 5,728,253 A | 3/1998 | Saito et al. | 156/345 |
| 5,739,051 A | 4/1998 | Saito | 438/16 |
| 5,770,523 A | 6/1998 | Hung et al. | 438/725 |
| 5,773,201 A | 6/1998 | Fujimara et al. | 430/329 |
| 5,807,761 A * | 9/1998 | Coronel et al. | 438/14 |
| 5,824,604 A | 10/1998 | Bar-Gadda | 438/725 |
| 5,846,373 A | 12/1998 | Pirkle et al. | 156/345 |
| 5,877,032 A * | 3/1999 | Guinn et al. | 438/9 |
| 5,877,407 A | 3/1999 | Cadet et al. | 73/24.01 |
| 5,882,489 A | 3/1999 | Besin et al. | 204/192.35 |
| 5,908,319 A | 6/1999 | Xu et al. | 438/725 |
| 5,965,934 A * | 10/1999 | Cheung et al. | 257/642 |
| 6,030,901 A | 2/2000 | Hopper et al. | |
| 6,037,255 A * | 3/2000 | Hussein et al. | 438/675 |
| 6,096,232 A * | 8/2000 | Hashimoto | 216/60 |
| 6,235,453 B1 | 5/2001 | You et al. | 430/329 |

FOREIGN PATENT DOCUMENTS

| | | |
|---|---|---|
| WO | WO/99/26277 | 10/1997 |
| WO | WO/97/37055 | 5/1999 |

OTHER PUBLICATIONS

Q. Han, M. Dahimene, P. Sakthivel, R. Mohonro, I. Berry, "Achieving Highly Selective Resist Strip and Residue Removal Over Dilelectrics Low–K", Future Fab International, vol. 7, pp219–222 (1999).

* cited by examiner

Primary Examiner—Benjamin L. Utech
Assistant Examiner—Kin-Chan Chen
(74) Attorney, Agent, or Firm—Watts, Hoffmann, Fisher & Heinke Co., L.P.A.

(57) ABSTRACT

A method for determining an endpoint for an oxygen free plasma stripping process for use in semiconductor wafer processing. The method comprises exciting a gas composition containing a nitrogen gas and a reactive gas to form the oxygen free plasma. The oxygen free plasma reacts with a substrate having a photoresist and/or residues thereon to produce emitted light signals corresponding to an oxygen free reaction product. The endpoint is determined by optically measuring a primary emission signal of the oxygen free reaction product at a wavelength of about 387 nm. The endpoint is determined when the plasma no longer reacts with the photoresist and/or residues on the substrate to produce the emitted light at about 387 nm, an indication that the photoresist and/or residues have been removed from the wafer. Secondary emission signals of the oxygen free reaction product at about 358 nm and 431 nm can also be monitored for determining the endpoint.

32 Claims, 8 Drawing Sheets

METHOD FOR DETECTING AN ENDPOINT FOR AN OXYGEN FREE PLASMA PROCESS

CROSS-REFERENCE TO RELATED APPLICATION

This application is a Continuation-In-Part application of, and claims priority from, U.S. patent application Ser. No. 09/368,553 entitled "Oxygen Free Plasma Stripping Process" filed on Aug. 5, 1999 now U.S. Pat. No. 6,281,135, hereby incorporated by reference in its entirety.

FIELD OF THE INVENTION

This invention relates generally to plasma ashing systems. More specifically, the invention relates to a method for detecting an endpoint for an oxygen free plasma process used for removing photoresist and/or residues from a substrate. In particular, the oxygen free plasma reacts with photoresist and/or residues to produce optical emission signals from the reaction products which are then optically monitored for determining the ashing endpoint.

BACKGROUND OF THE INVENTION

Ashing is a plasma process by which photoresist and residues are stripped or removed from a semiconductor wafer or the like upon exposure to a plasma. The ashing process generally occurs after an etching, implantation or deposition process has been performed in which a photoresist material is used as a mask for etching a pattern or depositing ions into the underlying substrate. The photoresist and residues remaining on the wafer after the etch or deposition process need to be removed. Typically, the plasma used for the ashing process is generated from a gas mixture containing oxygen as a component. The highly reactive oxygen containing plasma removes photoresist and residues by an oxidization reaction. The oxidation or combustion products resulting from the ashing operation are typically volatile components such as carbon dioxide and water vapor, and are carried away in a gas stream.

A problem with ashing is the accuracy in determining when the photoresist and/or residues have been removed. Accurate end point detection is critical to a high yield of high performance integrated circuits. Underetching or overetching is generally undesirable for numerous reasons well known to those skilled in the art. For instance, overetching causes linewidth variations which can affect device performance since the tolerance of the critical dimensions of the patterned circuit is very small.

One such technique in determining when the photoresist and/or residues have been removed is by in situ monitoring of the reaction between the photoresist and the plasma. This can be accomplished by a variety of means such as by optical emission spectroscopy, mass spectrometry, laser interferometry, ellipsometry and other techniques generally known to those skilled in the arts. Of these, optical emission spectroscopy is most preferred due to the non-intrusiveness, relative inexpense and durability compared to the other monitoring techniques. Many endpoint detection schemes based on optical emission spectroscopy have been defined for oxygen containing plasma ashing processes by monitoring particular spectral lines or regions determined by either a chemical constituent in the plasma and/or the emission signals produced by the reaction between the plasma and the photoresist and/or residues. The OH or CO functionalities are predominantly monitored since these are the primary emission signals produced during the oxygen containing plasma stripping process of photoresist and/or residues.

A problem that has surfaced recently with oxygen containing plasmas is that they are generally unsuitable for use with copper and most low k interconnects. Copper and low k materials are preferred for many reasons as device manufacturers transition beyond the 0.35 $\mu$m design rules. For example, copper has lower resistivity than aluminum which allows it to carry more current in a smaller area, thus enabling faster and denser integrated circuits or the like with increased computing power. Moreover, new insulating materials for interconnects, such as low k dielectrics, result in lower interconnect capacitance and crosstalk noise, thereby enhancing circuit performance. Low k dielectrics can generally be defined as those materials suitable for use in the manufacture of integrated circuits, or the like, having dielectric constants less than about 3.5. These low k dielectrics can be broadly grouped into four categories: organic, doped oxides, porous and TEFLON-like. Most low k dielectrics do not tolerate the presence of oxygen, especially in the form of plasma. It is well known that many of the low k dielectrics in the aforementioned categories are either etched at roughly the same rate as photoresist, or show better etch selectivity but suffer an increase in k value during exposure to oxygen containing plasmas. Even using very dilute oxygen mixtures, often used to slow the resist strip rate, has not overcome this problem for many of the low k materials.

Accordingly, the use of oxygen free plasmas have been found effective at removing photoresist and/or residues from low k materials. One such oxygen free plasma process for photoresist stripping is disclosed in the U.S. patent application Ser. No. 09/368,553 filed Aug. 5, 1999, entitled "Oxygen Free Plasma Stripping Process," which is incorporated herein by reference in its entirety. Optical methods for detecting the end point using the oxygen free plasmas for stripping photoresist and/or residues have yet to be defined. The existing methods of detecting the ashing endpoint are not adequate for detecting an endpoint during the use of the oxygen free plasma since the OH or CO functionalities are not sufficiently present to generate a signal having the desired magnitude for accurate endpoint detection.

Thus, there is a need for a method for detecting an ashing endpoint for an oxygen free plasma photoresist and/or residue removal process.

SUMMARY OF THE INVENTION

One object of the present invention is to provide a robust method for accurately determining the ashing endpoint for an oxygen free plasma stripping process. The inventive method, by precisely determining the ashing endpoint, advantageously avoids the problems associated with overetching or underetching. Moreover, the inventive method monitors a wavelength or a wavelength range having an emission signal that has a much higher signal to noise ratio than that previously observed from measuring the conventional transitions of OH or CO. As such, the ashing endpoint can be used in an intrinsically noisy system that includes, but is not limited to, radiation emitted from wafer heating lamps and radiation emitted from the plasma itself.

The present invention comprises the steps of placing a substrate having the photoresist and/or residues thereon into a reaction chamber. A gas composition containing a nitrogen gas and a selected one of a hydrogen bearing gas, a fluorine bearing gas and a fluorine-hydrogen bearing gas mixture is excited to form an oxygen free plasma. The oxygen free plasma reacts with the substrate having the photoresist and/or residues thereon to produce emitted light signals corresponding to reaction byproducts having unconventional transitions other than CO or OH. The light emission intensity signals resulting from the reaction byproducts are sequentially recorded over a period of time. The endpoint is determined at a time when the light emission intensity signals of the reaction product are no longer detectable. The reaction produces, among others, oxygen free compounds or oxygen free radicals which emit at a primary signal at a wavelength of about 387 nm and secondary emission signals at about 358 nm and at about 431 nm.

In one embodiment, emitted light within a wavelength range that includes the primary emission signal at about 387 nm is recorded by a spectrometer, such as by a CCD based spectrometer. When the intensity of the emission signal at about 387 nm within that wavelength range is no longer detectable or reaches a steady state below a threshold value, the ashing endpoint is determined by an appropriate algorithm and the plasma is turned off to prevent overetching. Preferably, the wavelength range includes the secondary emission signals at about 358 nm and about 431 nm. The predetermined threshold value represents contributions to the emission signal at primary and secondary wavelengths that are not caused by the reaction between the photoresist, residues and plasma.

In another embodiment, a specific wavelength of about 387 nm is optically measured, such as by a monochromator. A first emission intensity signal at the primary emission signal of about 387 nm is measured prior to reacting the plasma with the photoresist and/or residues. The first emission intensity signal represents the background radiation which comprises radiation from sources such as the plasma, and the wafer heating lamps. Preferably, a blank or dummy wafer is run during measurement of the first intensity signal. The substrate having photoresist and/or residues thereon is then exposed to reactive species of the plasma to generate a second emission intensity signal at about 387 nm. Preferably, the reactive species of the plasma are electrically neutral. The photoresist and/or residues react(s) with the reactive species of the oxygen free plasma to produce unconventional volatile products, products that are very different from those produced during exposure to an oxygen containing plasma. These products emit the primary light signal at about 387 nm and secondary light signals at about 358 nm and about 431 nm. The method of detecting an ashing endpoint further involves measuring the second emission intensity signal at the primary light signal of about 387 nm as the plasma is exposed to the substrate. Alternatively, the secondary light signals can be measured for determining endpoint. The ashing endpoint of the plasma stripping process is determined by comparing the first intensity signal with the second intensity signal wherein the endpoint is detected when said first and second intensities are about the same. Consequently, the ashing endpoint is determined when the reaction products are no longer being evolved, an indication that the photoresist and/or residues are no longer present in sufficient quantities to produce a detectable emission signal.

The present invention can be used to determine the ashing endpoint for any oxygen free plasma process wherein the conventional transitions of CO and OH are not sufficiently present to generate a detectable light signal having the desired magnitude for accurate endpoint detection. The particular components of the gas composition are selected by their ability to form a gas and a plasma at plasma forming conditions, and often by the lack of damage to low k materials. Preferably, the gas composition for generating the oxygen free plasma contains nitrogen gas and a reactive gas. Preferably, the reactive gases are a selected one of a hydrogen bearing gas, a fluorine bearing gas and a fluorine-hydrogen bearing gas mixture to form the oxygen free plasma. In cases where no nitrogen is present as a mixture of any of the reactive gases, i.e. the fluorine bearing compound or the hydrogen bearing compound, nitrogen is added separately as a process gas. Preferably, the components are combined and added to the plasma asher as a gas.

Preferably, the methods for optically measuring the emission signals during reaction of the plasma with the photoresist and/or residues is by the use of a light detector. Equipment suitable for use in present invention include a monochromator, a spectrometer, or the like. Other spectroscopic methods suitable for use in the present invention will become apparent to those skilled in the art in view of this disclosure. The invention is not intended to be limited to any particular optical emission spectroscopy means or filters. Generally, the differences between the various spectrometers is the range of wavelength monitored and the differentiation capability for distinguishing background radiation from the emitted species of interest. It is well within the skill of those in the art to determine how the various spectrometer configurations or the like can be used to differentiate the background radiation from the radiation emitted from the reaction of the plasma, photoresist and residues.

These and other objects, advantages and features of the invention will become better understood from the detailed description of the invention which is described in conjunction with the accompanying drawings.

DETAILED DESCRIPTION OF PREFERRED EMBODIMENTS

The present invention is generally directed to a method for detecting an end point of a plasma stripping process that uses an oxygen free plasma for removing photoresist and/or residues from a substrate such as semiconductor wafers or the like. The oxygen free plasma is generated by exciting oxygen free process gases to produce a reactive plasma that reacts with the photoresist and/or residues to produce, among others, volatile byproducts. The byproducts are unconventional in that they do not include the conventional transitions observed with oxygen containing plasmas, i.e. those transitions associated with OH and CO. The oxygen free plasma of the present invention requires the presence of nitrogen in the oxygen free gas. Nitrogen can be added as part of a mixture of the reactive gases or as a separate process gas. In one embodiment, the endpoint is determined by monitoring a wavelength range that includes a specific volatile byproduct that emits a primary light signal at about 387 nm produced by a reaction between the oxygen free plasma and the photoresist and/or post etch residues. In another embodiment, the endpoint is determined by monitoring the specific wavelength of about 387 nm. Optionally, secondary emission signals at wavelengths of about 358 nm and 431 nm can be monitored in combination with the primary emitted signal at about 387 nm or individually. Preferably, the means for monitoring the reaction of either embodiment is by optical emission spectroscopy, such as by use of a monochromator or spectrometer or other spectral monitors. Generally, monochromators are used to isolate a narrow portion of a spectrum whereas spectrometers are capable of measuring a wider range of wavelengths.

The reaction between the plasma and the photoresist and/or residue produces, among others, oxygen free compounds or oxygen free radicals which emit at least one detectable primary light signal at the wavelength of about 387 nm and secondary emission signals at wavelengths of about 358 nm and 431 nm. Preferably, the method of endpoint detection includes, among others, the step of monitoring a wavelength range that includes the primary emission signal at the wavelength of about 387 nm, such as by a spectrometer. Preferably, the wavelength range or wavelengths monitored includes the secondary emission signals at about 358 nm and about 431 nm. The secondary emission signals have a lower signal intensity than the primary emission signal and are believed to be generated by the same reaction byproduct that generates the primary emission signal at about 387 nm. The endpoint of the ashing process is determined when the light emission intensity signal from the reaction between the plasma and the photoresist and/or residue on the substrate at about 358 nm, 387 nm or 431 nm are no longer detected. Once the emission intensity is no longer detected from the reaction, at especially the primary wavelength at about 387 nm, a signal is sent to a control unit of a plasma asher indicating the end of the ash step.

A predetermined threshold value is generally decided by the amount of background radiation at about 387 nm or, if a CCD based spectrometer is used, over a range of wavelengths. The background radiation can originate from numerous sources, including but not limited to, radiation emitted from the plasma, radiation produced from a reaction between the plasma and impurities in the reaction chamber, stray light or radiant energy emitted from lamps that may be used to heat the wafers during processing.

For a plasma asher configured with the monochromator, the amount of background radiation may be readily determined by running blank or dummy wafers through the plasma reactor and optically measuring the wavelength that includes the emission signal of interest. Using blank or dummy wafers to detect the background radiation is preferred since the conditions resulting from the use thereof are representative of actual conditions used during processing of coated wafers. The background radiation can then be used for deciding a threshold value wherein the ashing endpoint is determined when the emission signal reaches the predetermined threshold value.

For a plasma asher configured with a spectrometer, such as a CCD based spectrometer, the spectrometer time sequentially records an emission spectrum that includes the emission signal corresponding to the products produced from the reaction between the oxygen free plasma and the photoresist and/or residues. Preferably, the wavelength at about 387 nm is monitored and corresponds to the primary signal of interest in the present invention. Secondary emission signals at wavelengths of about 358 nm and 431 nm can also be used to the determine endpoint in combination with the primary emission signal or individually. The background radiation over the wavelength range can be removed by methods known to those skilled in the art from the real time emission spectra during the ashing processing. Thus, the need to run blank or dummy wafers as discussed above with regard to a monochromator is eliminated. As such, an end point of the ashing process may be detected when the emission intensity at about 387 nm reaches a steady state at about zero intensity.

The particular components of the oxygen free plasma gas are selected by their ability to form a gas and a plasma at plasma forming conditions, and often by their lack of damage to low k materials. The oxygen free plasma suitable for use in the present invention includes, among others, nitrogen. Preferably, the components are combined and added to the plasma asher as a gas mixture. The oxygen free plasma gas primarily reacts with carbon and other atoms in the photoresist compounds and/or post etch residues to form volatile compounds at conditions present in a plasma reaction chamber. Moreover, the oxygen free plasma reacts with those traditionally hard to remove post etch residues that usually contain silicon embedded in the residue.

A preferred oxygen free plasma gas composition, particularly when used with integrated circuits employing copper and low k dielectrics, is a mixture of a fluorine bearing gas, a hydrogen bearing gas and nitrogen gas. This combination is very efficient in generating sufficient reactive species to increase the selectivity of the photoresist strip rate to the dielectric etch strip rates on a substrate having photoresist and a dielectric layer exposed and/or underlying the photoresist layer.

Preferred fluorine bearing compounds include those compounds that generate fluorine reactive species when excited by the plasma. Preferably, the fluorine bearing gas is selected from the group consisting of a compound having the formula $C_xH_yF_z$ wherein x ranges from 1 to 4, y ranges from 0 to 9 and z ranges from 1 to 10, $NF_3$, $F_2$, and $SF_6$. Other fluorine bearing compounds will be apparent to one of ordinary skill in the art in view of this disclosure. More preferably, the fluorine bearing compound is $CF_4$ or $CHF_3$.

Preferably, the fluorine compounds are less than about 10 percent of the total volume of the composition to maximize etch selectivity. It has been found that when the fluorine bearing compounds are greater than about 10 percent by volume, polymerization can occur, making the photoresist more difficult to remove. Moreover, it was unexpected to find the enhanced removal rates when using a fluorine bearing gas in combination with a hydrogen bearing gas. Typically, the mixing of hydrogen bearing gas with a fluorine bearing gas results in the formation of hydrogen fluoride which is believed to be caused by scavenging of fluorine radicals by hydrogen. Hydrogen fluoride in the plasma is known to those skilled in the art to lower removal efficiency of traditional dielectrics, such as silicon dioxide. Thus, it was unexpected to observe an increase in removal efficiency of residues in the presence of low k dielectrics.

The hydrogen bearing compounds include those compounds that contain hydrogen, for example, hydrocarbons, hydrofluorocarbons, hydrogen gas, hydrogen gas mixtures or the like. Suitable hydrogen gas mixtures include mixtures of a hydrogen bearing compound and nitrogen or, alternatively, a mixture of a hydrogen bearing compound and a nonreactive gas such as argon neon, or helium. The hydrogen bearing compounds used have the critical role of increasing selectivity of the stripping process.

Preferred hydrogen precursor gases are those that exist in a gaseous state and release hydrogen to form reactive hydrogen species such as free radical or hydrogen ions under plasma forming conditions. The gas may be a hydrocarbon that is unsubstituted or may be partially substituted with a halogen such as bromine, chlorine or fluorine, or with oxygen, nitrogen, hydroxyl and amine groups. Preferably, the hydrocarbon has at least one hydrogen and from one to twelve carbon atoms, and more preferably has from three to ten carbon atoms. Examples of suitable hydrogen bearing gases include methane, ethane, ammonia and propane.

Preferred hydrogen gas mixtures are those gases that contain hydrogen gas and an inert gas. Examples of the inert gas include argon, nitrogen, neon, helium or the like. Especially preferred hydrogen gas mixtures are so-called forming gases which consist essentially of hydrogen gas and nitrogen gas. Particularly preferable for use in the present invention is a forming gas wherein the hydrogen gas ranges in an amount from about 3 to about 5 percent by volume of the total forming gas composition, the limitation of which being due only for safety considerations during operation of the plasma asher.

In cases where no nitrogen is present as a mixture of any of the reactive gases, i.e. the fluorine bearing compound or the hydrogen bearing compound, nitrogen is added separately as a process gas.

Alternatively, other oxygen free plasmas gases can be used to generate the plasma. As discussed above, the particular components of the other oxygen free plasma gases are selected by their ability to form a gas and a plasma at plasma forming conditions and contain nitrogen as one of the process gases or as a mixture therewith. For example, the gas could be a mixture of two or more gases or a individual gases. The invention is not intended to be limited to any particular nitrogen containing oxygen free gas plasma. In particular, the oxygen free plasma reacts with the photoresist and/or residues to produce reaction product different from those typically produced with oxygen containing plasmas. The wavelength or wavelength range including the corresponding primary emission signal at about 387 nm is then monitored for determining the ashing endpoint. Other oxygen free gas plasma compositions suitable for use in the present invention will be apparent to those skilled in the art in view of this disclosure.

The endpoint detection method will remain the same independent of the plasma processing variables. However, the removal rate can also be further optimized as is known to those skilled in the art. For example, the plasma chamber pressure can be changed from about 0.5 torr to about 10 torr, the power can be adjusted from about 500W to about 2000W, the wafers may be step-wise heated from about 80° C. to about 350° C. during ashing or the total gas flow rates can be adjusted from about 500 sccm to about 9000 sccm. The oxygen free plasma generated under any of these conditions will react with photoresist and/or residues to produce an emission signals at 358 nm, 387 nm, and 431 nm which are then subsequently monitored individually or in combination to determine the endpoint of the ashing step. Preferably, the primary emission signal at about 387 nm is monitored for determining the ashing endpoint.

Photoresists are generally organic photosensitive films used for transfer of images to an underlying substrate. The present invention is generally applicable to stripping those photoresists used in g-line, i-line, DUV, 193 nm, and 157 nm applications. This includes, but is not limited to, novolaks, polyvinylphenols, acrylates, acetals, ketals, cyclic olefins or the like. Other suitable photoresist formulations will be apparent to those skilled in the art in view of this disclosure. The photoresist may be positive acting or negative acting depending on the photoresist chemistries and developers chosen.

The post etch and post deposition residues are believed to be photoresist that have undergone a chemical change during earlier processing steps typically making the residue more resistant to the stripping plasma. The post etch residues include those residues known as sidewall polymer deposits. It is believed the chemical change occurs as a result of an earlier dielectric etching step by which the components of the plasma reactor lining or the wafer react with photoresist to form post etch residues or the chemical change may occur from the reaction of species generated during plasma processing.

In general, the reactive species formed by generating the oxygen free plasma in the presence of nitrogen differ from those reaction products typically formed in oxygen containing plasmas. The reactive species generated by. the plasma gas mixture removes the photoresist and/or residues react to form volatile products. Other methods of residue removal using the plasma include weakening adhesion to the substrate or by rendering the residue water removable. The residues can then be subsequently removed in a deionized water rinse step. The stripping process continues until the volatile reaction products from the reaction between the photoresist and/or residues are no longer evolved. The reaction byproduct of interest in the present invention is the one that emits the primary light signal at about 387 nm. Alternatively, secondary emission signals at about 358 nm and about 431 nm can be used in combination with, or independently of the emission signal at about 387 nm for determining the ashing endpoint.

Plasma asher devices particularly suitable for use in the present invention are downstream plasma ashers, such as for example, those microwave plasma ashers available under the trade name GEMINI ES and commercially available from Eaton Corporation. Portions of the microwave plasma asher are described in U.S. Pat. Nos. 5,498,308 and 4,341,592, and PCT International Application No. WO/97/37055, herein incorporated by reference in their entireties. The invention is not limited to any particular plasma asher in this or in the following embodiments. For instance, an inductively coupled plasma reactor can be used.

Figure 1:
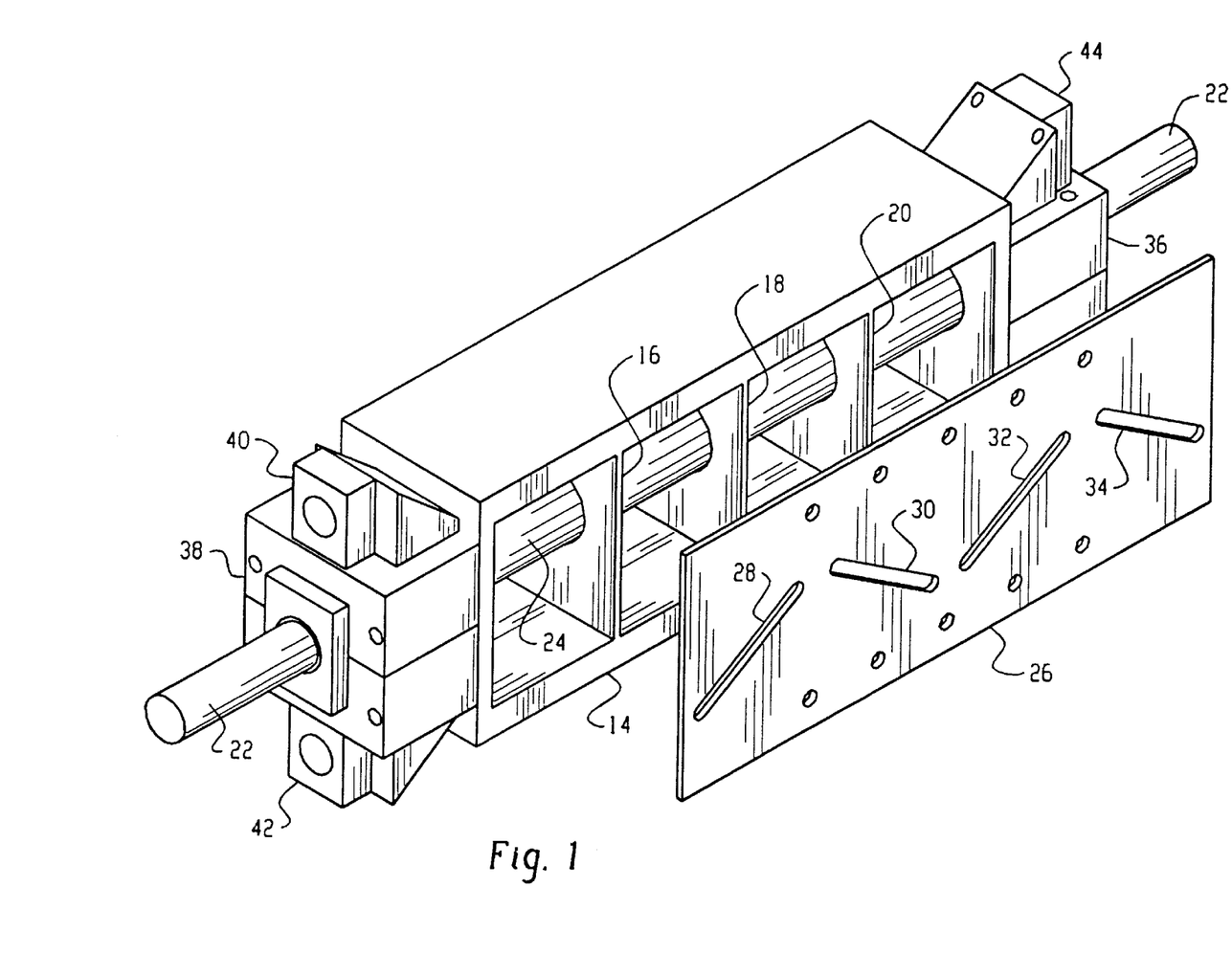
FIG. 1 shows a perspective view of a microwave enclosure for use in a plasma asher.
Figure 2:
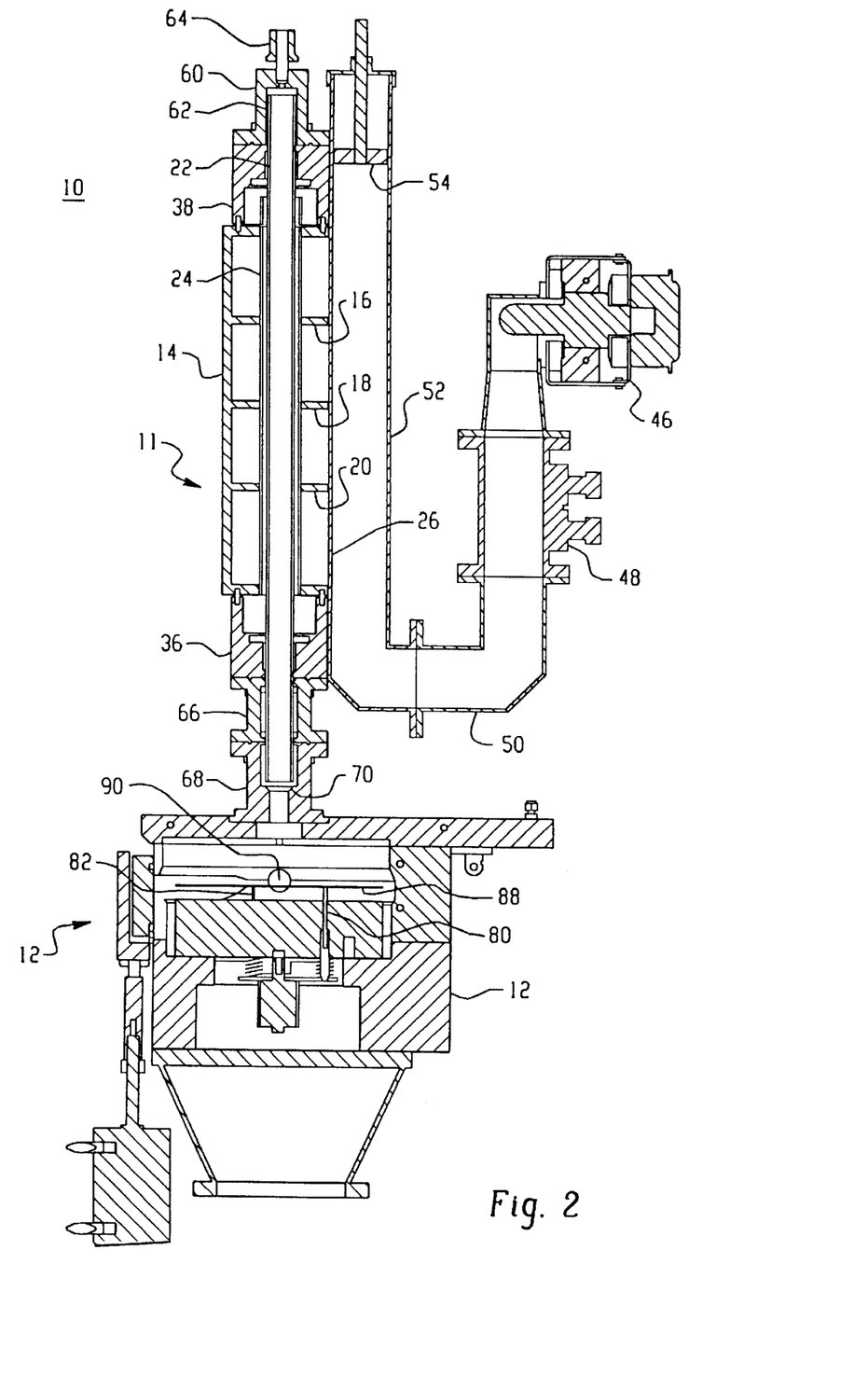
FIG. 2 shows a cross sectional view which schematically shows a plasma reaction chamber suitable for use in the present invention.

Referring now to FIGS. 1 and 2 in particular, there is depicted a microwave plasma asher that is generally designated by reference numeral 10 and is suitable for practicing the method of photoresist and/or post etch residue removal by treatment with oxygen free plasma. The illustrated plasma asher includes a plasma generating chamber 11 and a plasma reaction chamber 12. The plasma generating chamber includes a microwave enclosure 14. The microwave enclosure is a rectangular box partitioned into lengthwise sections 16, 18, and 20 having plasma tube 22 passing therethrough. Each partition has an opening through which the plasma tube passes. Each section is fed with microwave energy. Thus, each section is a relatively short cavity to the incoming microwave energy, promoting the formation of modes having azithumal and axial uniformity. Outer tube 24 surrounds the plasma tube inside the cavity. The outer tube is slightly separated from the plasma tube and air under positive pressure is fed between the two tubes to provide effective cooling of the plasma tube. Tube 24 is preferably made of sapphire. Other plasma tube materials such as quartz, alumina or alumina coated quartz can be used.

The openings in partitions 16, 18, and 20 through which the concentric tubes are fed are made larger than the exterior dimension of the plasma tube. There is microwave transmission through such openings that causes a plasma to be excited uniformly in the tube. Such transmission helps reduce thermal gradients in the plasma tube. If an outer tube is not used (cooling provided in some other manner) the openings in the partition are sized so that there is a space between the plasma tube and the partition to provide such microwave transmission. FIG. 1 shows the space between the outer tube and the partition.

Also shown is an iris plate 26 that covers the open side of the microwave structure and is effective to feed microwave energy into adjacent sections. Plate 26 is a flat metallic pate having irises 28, 30, 32, 34, through which the microwave energy is fed.

Microwave traps 36 and 38 are provided at the ends to prevent microwave transmission. Such traps may be of the type disclosed in U.S. Pat. No. 5,498,308, which is incorporated herein by reference. Air seals/directional feeders 40 and 42 are provided for admitting cooling air and feeding it to the space between the concentric tubes. Air seals/directional feeder 44 is shown at the outlet end and a fourth such unit is present but is not seen.

Magnetron 46 provides microwave power fed through coupler 48 to a waveguide supplying $TE_{10}$ mode, having mutually perpendicular sections 50 and 52. The length of waveguide section 52 is adjustable with moveable plunger 54. The bottom plate of waveguide section 52 is iris plate 56, which couples microwave energy into partitioned microwave structure 14, through which the plasma tube 22 extends; thus, a plasma is excited in the gas flowing through the plasma tube.

Referring again to FIG. 2, it is seen that end cap 60 abuts microwave trap 38, and fitting 64 having a central orifice for admitting gas to the plasma tube extends into the end cap. The gas supply is regulated by an external flow box (not shown).

The plasma tube is supported at this end by "o" ring 62 in the end cap. The outer tube 24 is supported at its ends by abutment against microwave traps 36 and 38. Spacer 66 is present to provide the proper spacing in relation to the process chamber. The other end of the plasma tube is found in end member 68, and has an orifice 70 for emitting gas into the process chamber.

Preferably, the microwave enclosure 14 is dimensioned to support the rectangular $TM_{110}$ mode and the enclosure 14 may have a square cross section. The dimensions of the cross sections are such that the $TM_{110}$ mode is resonant. The length of each section is less than $\lambda_g/2$ where $\lambda_g$ is the guide length within the cavity of the $TE_{104}$ mode.

The plasma reaction chamber 12 includes wafer support pins 80 and 82, which support wafer 88, to be processed. A chuck (not shown) may alternatively be used. Heating may be accomplished by an array of tungsten halogen lamps (not shown) positioned below the wafer. Preferably, the substrate is heated from about 80° C. to about 350° C. during ashing. More preferably, the substrate is step-wise heated by incrementally increasing the temperature. Heating has been found to increase the reaction rate of the plasma with the photoresist and/or residues and consequently, increase the throughput. One or more baffle plates (not shown) may be present above the wafer to promote even distribution of the plasma to the wafer surface.

A side wall of the reaction chamber includes a optical port opening 90 made of a transparent material such as quartz or sapphire. The opening is configured and located such that an optical path approximately parallel to the wafer plane is formed. The emission spectra of the oxygen free plasma are passed through the opening. Collection optics(not shown) may be arranged outside and behind the window to collect the emission spectra thus passed. A spectrometer or monochromator, (generally shown as 92 in FIG. 3) is further arranged to receive light from the collection optics. Optical emission spectroscopy apparatus and techniques are generally well known and discussed in numerous publications. In one embodiment, the optical emission spectroscopy is by a spectrometer, such as a CCD (charge couple device) based spectrometer, that time sequentially records a wavelength range and converts the emission spectra into analog signals for subsequent analysis. Optionally, narrow band filters can be used to permit evaluation of specific ranges of the wavelength of interest on a light detector such as the CCD or a photodiode array. The spectrometer time sequentially converts light signals emitted during the ashing process into an electrical analog signal which can then be analyzed using methods known to those skilled in the art to produce a desired output. Preferably, the data is viewed in real time. Preferably, the data is viewed in graphical form showing the time evolution of the light intensity emitted during plasma processing for the wavelength range of interest.

Alternatively, other optical detectors can be used. For instance, as discussed above, a monochromator can be used to collect the data. As is known to those skilled in the art the monochromator can be configured with a photomultiplier tube, a photodiode or the like to record the emission signal of a narrow spectrum at about 387 nm.

These optical emission spectroscopy devices and suitable configurations within a plasma reaction chamber will be apparent to those skilled in the art in view of this disclosure. Examples of monochromators suitable for use in the present invention is model no. EP200MMD commercially available by Verity Corporation, U.S. Examples of scanning monochromators suitable for use in the present invention include model no. EP200SMD commercially available by Verity Corporation. Examples of CCD based spectrometers suitable for use in the present invention are Model Nos. SD1024 commercially available by Verity Corporation and series PC2000 CCD spectrometers commercially available from Ocean Optics, U.S. Examples of photodetector arrays suitable for use in the present invention is model no. SPM9001 commercially available by Prema Company, Germany. The method of detecting an endpoint for an oxygen free plasma process requires the capability of monitoring a change in the emitted intensity signal at about 387 nm. Optionally, as discussed above, the secondary wavelengths at about 358 nm and about 431 nm corresponding to the reaction byproduct at about 387 nm can be monitored in combination or individually.

Figure 3:
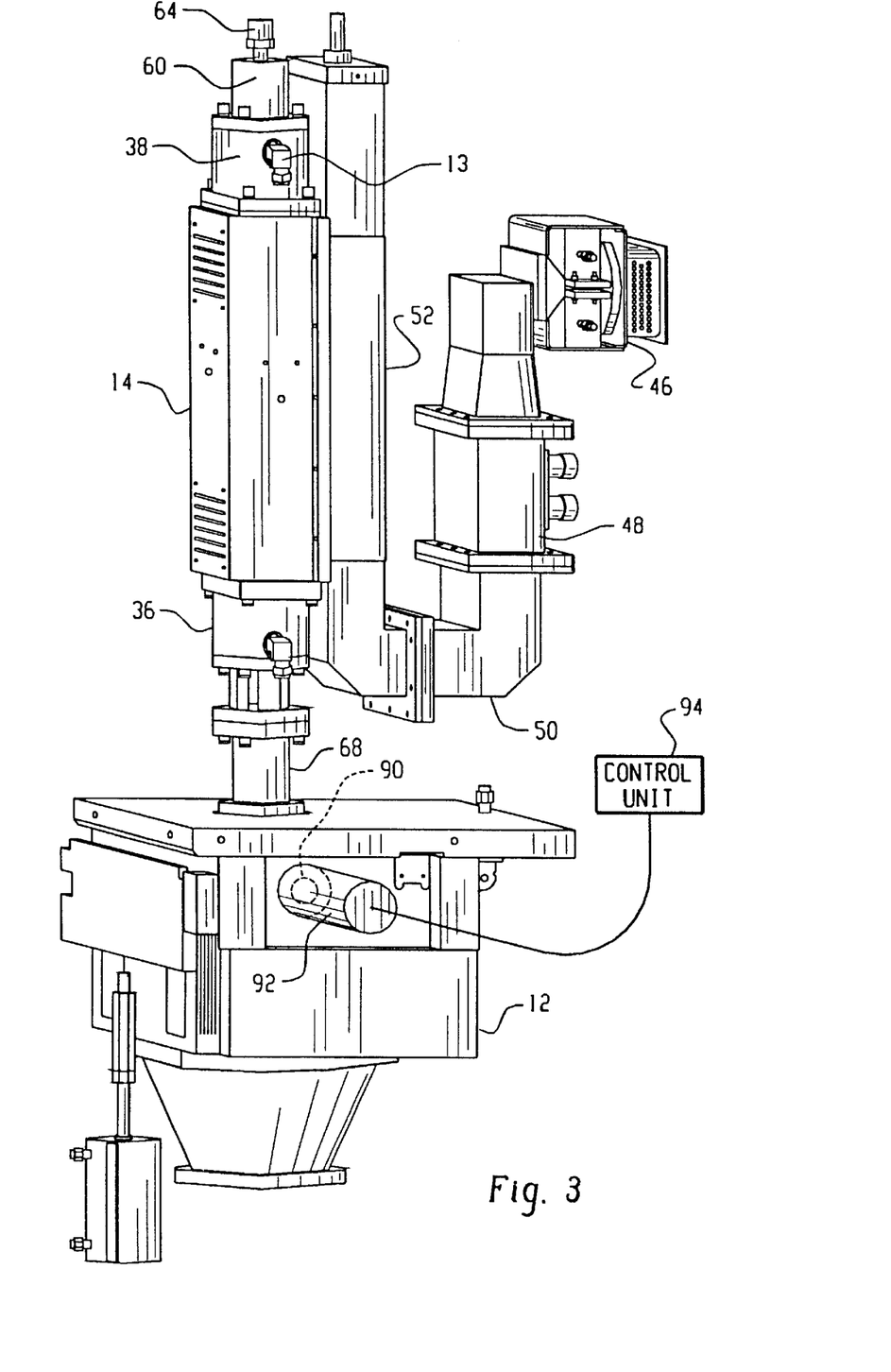
FIG. 3 shows a perspective view of the plasma asher depicted in FIG. 2.

Referring to FIG. 3, an exterior view of the device is shown. The reference numerals in FIG. 3 correspond to those used in the other Figures.

In operation, the semiconductor wafer 88 with photoresist and/or post etch residues thereon is placed into the reaction chamber 12 on wafer support pins 80 and 82. The wafer is preferably heated to accelerate the reaction of the photoresist and/or post etch residues with the plasma. The pressure within the reaction chamber is reduced. Preferably the pressure is maintained between about 1 torr to about 5 torr. An excitable oxygen free gas that includes nitrogen as one of its components is fed into plasma tube 22 of the plasma generating chamber 11 via a gas inlet 13 (as shown in FIG. 3). Each section 16, 18, 20 is fed with microwave energy to excite a plasma in the plasma tube, which plasma is comprised of electrically neutral and charged particles. The charged particles are selectively removed before the plasma enters the reaction chamber. The excited or energetic atoms of the gas are fed into the reaction chamber and react with the photoresist and/or post etch residues. The oxygen free plasma reacts with the photoresist and/or post etch residues to form volatile products. A specific reaction product is monitored optically by optical emission spectroscopy means 92, such as the spectrometer, monochromator or the like. The volatile gases are continuously swept away from the wafer surface by a gas sweep within the reaction chamber such that it passes by the optical port 90.

For a plasma asher configured with a CCD based spectrometer, the CCD spectrometer time sequentially records an emission spectrum that includes the emission signal corresponding to about 387 nm as it is being evolved. The wavelength range of the emission spectrum monitored is determined by the type of CCD spectrometer used and the presence of any filters used to eliminate certain wavelength emissions from reaching the CCD spectrometer. The CCD spectrometer configuration simultaneously records the background radiation and the radiation from the emitted species during the ashing process. Using standard algorithms known to those skilled in the art, the background radiation can be subtracted from the radiation resulting from the reaction of the plasma with the photoresist and/or residues. Once the emission peak records a change in intensity values and a steady state at a minimum predetermined level is reached, the removal of photoresist and/or residues is complete, a signal is then sent to a control unit 94 and the plasma is turned off. The vacuum is released and the processed wafers may be removed from the reaction chamber. An optional deionized water rinse is used to remove any remaining residue on the stripped wafer.

In a plasma asher with a monochromator, blank uncoated wafers are first exposed in the reaction chamber and a first emission signal at about 387 nm is measured. The first emission signal represents the background radiation as discussed above. Next, substrates having photoresist and/or residues thereon are exposed to the oxygen free plasma in the reaction chamber. A second emission signal emitted at about 387 nm is recorded by the monochromator. The background radiation of the first emission signal is subtracted from the second emission signal. When the second emission signal at about 387 nm reaches a steady state and is about the same or below the first emission signal, the ashing endpoint has been reached and a signal is then sent to a control unit 94 in the plasma asher and the plasma is turned off. The vacuum is then released and the processed wafers are removed from the reaction chamber. An optional deionized water rinse is then used to remove any remaining residues on the stripped wafer.

Other monochromator, spectrometer or like configurations and operations thereof for monitoring the reaction byproducts at the primary and secondary emission signals of about 358 nm, 387 nm and 431 nm will be apparent to those skilled in the art in view of this disclosure.

The following examples are detailed description of methods for detecting an ashing endpoint during use of an oxygen free plasma for removing photoresist. The detailed methods fall within the scope of, and serve to exemplify, the more generally described methods set forth above. The examples are presented for illustrative purposes only, and are not intended to limit the scope of the invention. For instance, the plasma asher could be configured with other spectrometers or monochromators to monitor the emission signals including the primary emission signal at about 387 nm.

EXAMPLE 1

In the following example, a DUV photoresist was coated onto multiple silicon wafers at 3000 rpm. The photoresist is available under the trade name UV6-1.0 and commercially available from the Shipley Company. After baking each wafer for 45 seconds at 130° C. on a vacuum hotplate a tack free photoresist film was obtained having a thickness of about 10,000 angstroms. The photoresist film was then exposed to microwave plasma using a Fusion Gemini ES Plasma Asher available from Eaton Corporation with the reaction chamber configured to include a CCD spectrometer. The plasma chamber power was set at 1800W with a chamber pressure of 3.0 torr. The wafers were exposed to a plasma generated from forming gas with a gas flow rate of 2500 sccm. The forming gas used was a mixture of hydrogen and nitrogen gases wherein the hydrogen gas was 3% by volume of the total forming gas mixture. The wafers were heated to a temperature of 300° C. The light emitted during the plasma reaction with the photoresist was collected by a CCD spectrometer configured behind a window in a sidewall of the reaction chamber forming an optical path approximately parallel to the wafers surface. The wavelength spectrum between 200 and 500 nm was recorded with a CCD spectrometer wherein the CCD spectrometer collected the emission signal for 50 ms of every second of the plasma process.

Figure 4:
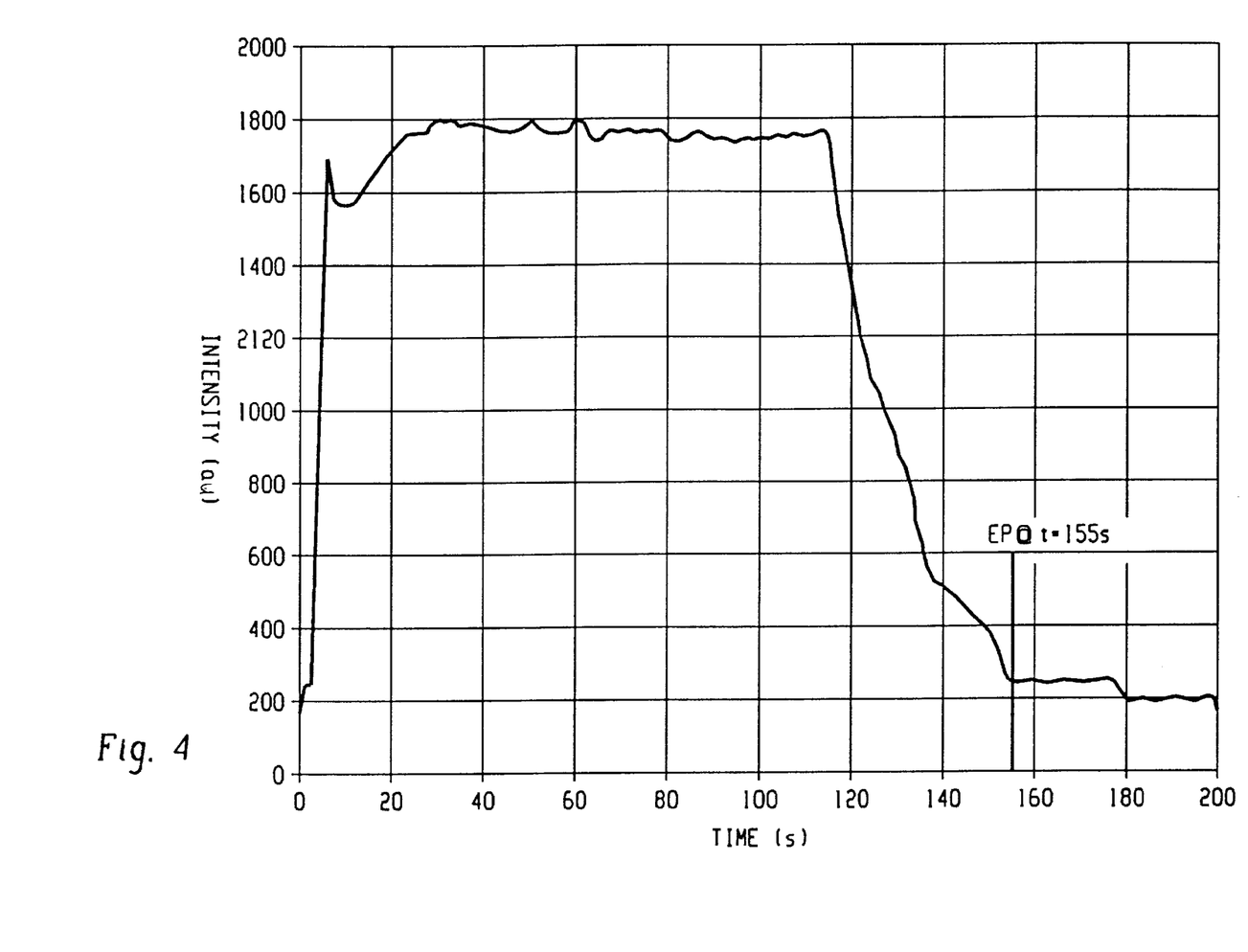
FIG. 4 is a 2-dimensional graphical view showing a time evolution of a light intensity emitted at 387 nm during an ashing process with an oxygen free plasma comprising a hydrogen bearing gas monitored by a CCD based spectrometer.
Figure 5:
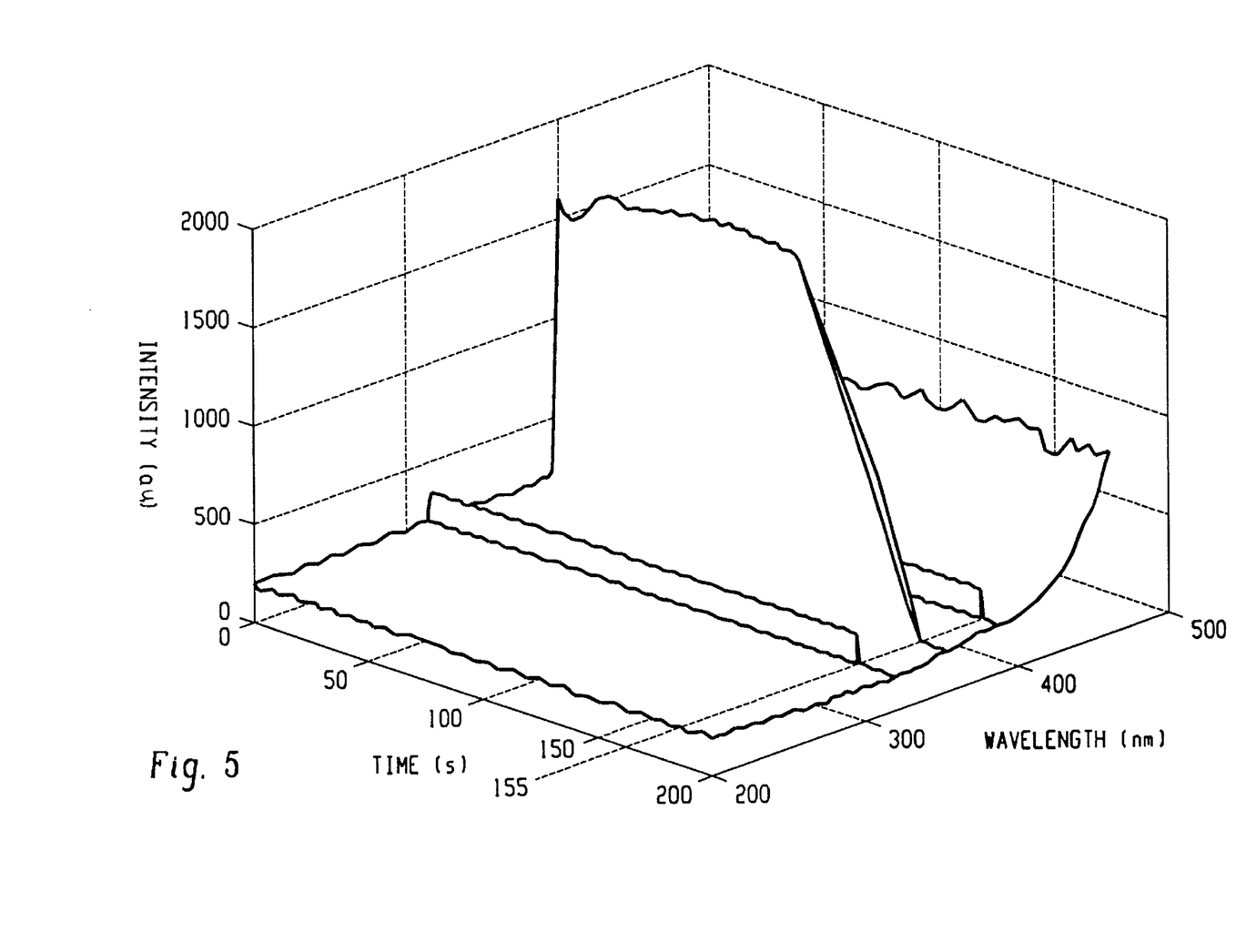
FIG. 5 is a 3-dimensional graphical view showing the time evolution of light intensity emitted from 200 nm to 500 nm during the ashing process as shown in FIG. 4.

FIG. 4 and 5 are graphs showing the time evolution of light intensity emitted from 200 nm to 500 nm during ashing with an oxygen free plasma. Although the data shown in FIG. 4 was collected with a CCD based spectrometer, FIG. 4 is illustrative of the type of data obtained with the plasma asher configured with a monochromator without background radiation subtraction. A pronounced signal is observed at about 387 nm. The data suggest an ashing endpoint occurs at about t=155. That is, after 155 seconds of ashing, the reaction between the plasma, and the photoresist and/or post etch residues has been completed. No detectable emission is recorded after 155 seconds and the plasma is turned off to prevent overetching. The data in this example suggests that the threshold at 387 nm can be set at 250 intensity emission units. In a production environment, using similar conditions, once the emission signal at about 387 nm reaches a steady state below the threshold value, a signal is sent to a control unit which turns off the plasma. Thus, precise determination of the ashing endpoint can be made. FIG. 5 depicts a gradual increase in emission intensity as the wavelength is increased from about 400 nm to 500 nm and is caused primarily by the broadband radiation caused by the lamps used to heat the wafers during processing. FIG. 5 also shows the secondary signals at about 358 nm and 431 nm.

EXAMPLE 2

In this example, multiple silicon wafers were coated with a thin layer of a bottom anti-reflective layer and then with 5000 angstroms photoresist and exposed under the same conditions as in Example 1 to an oxygen free plasma generated from process gases including fluorine bearing gas and nitrogen gas. The fluorine bearing gas was $CF_4$.

Figure 6:
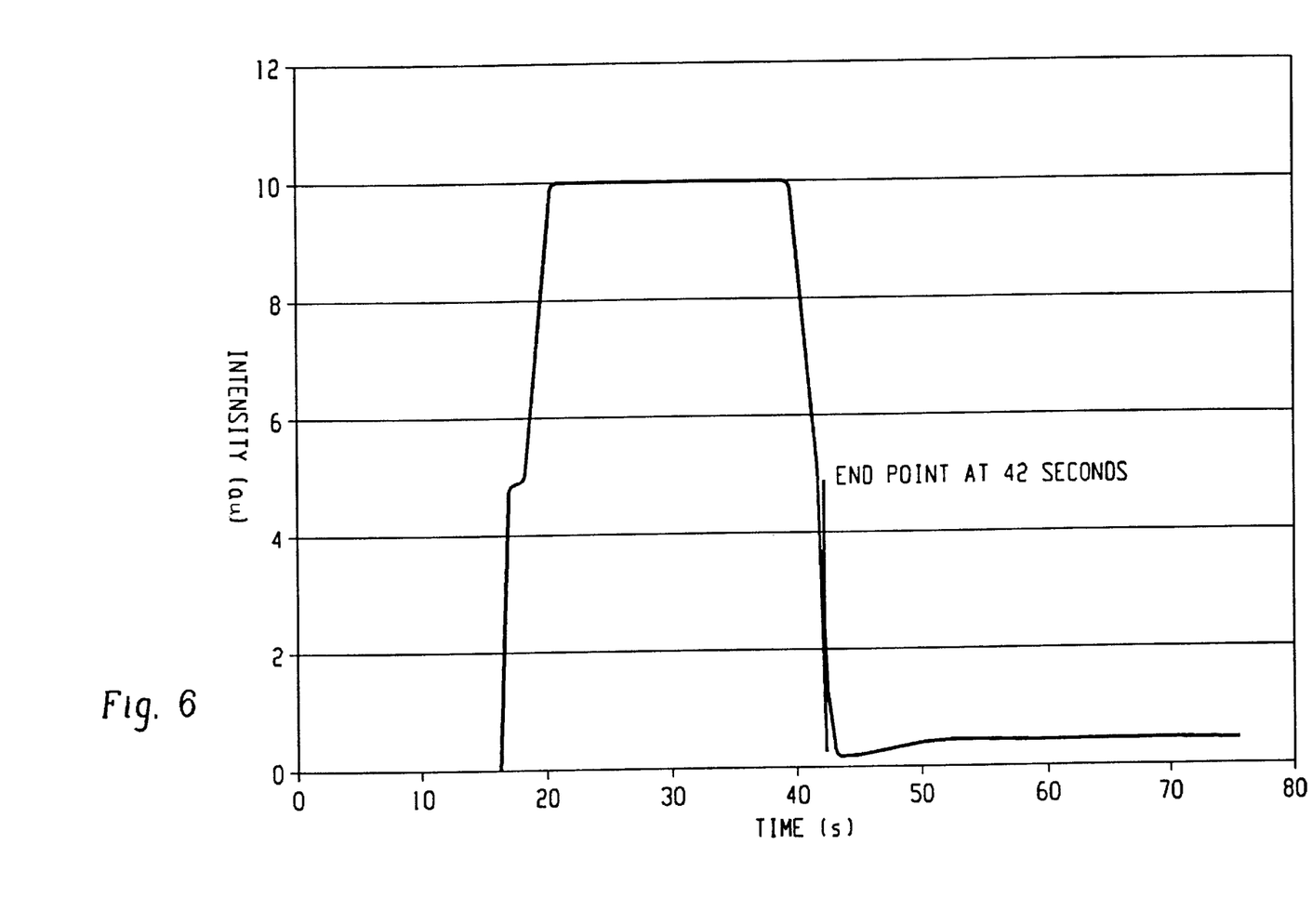
FIG. 6 is a 2-dimensional graphical view showing a time evolution of a light intensity emitted at 387 nm during an ashing process with an oxygen free plasma comprising a fluorine bearing gas monitored by a CCD based spectrometer.
Figure 7A:
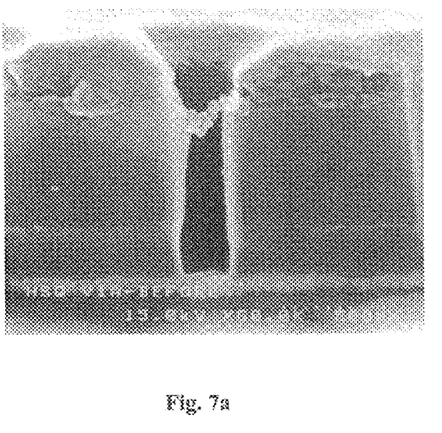
FIG. 7 are pictorial views of scanning electron micrographs showing a cross sectional and top down view of a contact hole before and after an oxygen free plasma stripping process in accordance with the present invention.
Figure 7B:
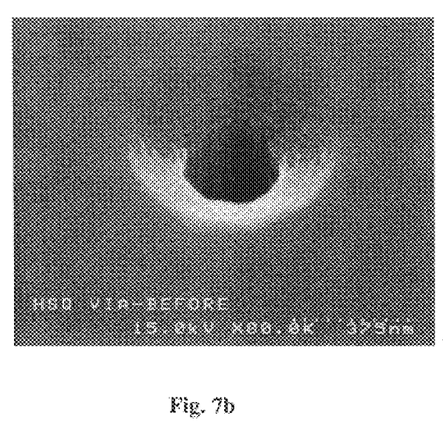
Figure 7C:
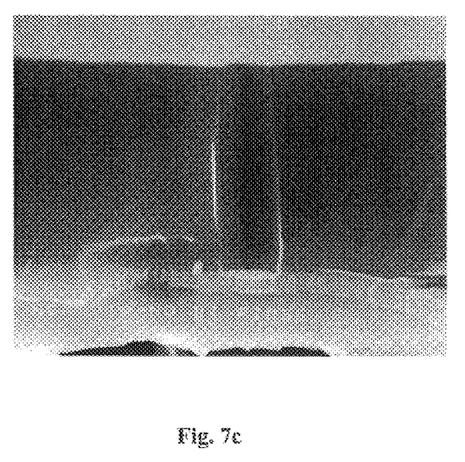
Figure 7D:
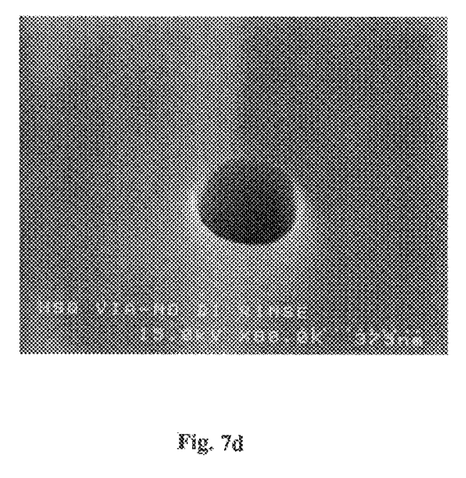

FIG. 6 is a graph showing the emission intensity as a function of time monitored at a wavelength at about 387 nm measured during the plasma process. The endpoint occurs at about 42 seconds, an indication that the photoresist has been removed and the plasma should be turned off to prevent overetching. Comparing the data shown in each example, it is clear that the fluorine bearing gas is more efficient in photoresist removal requiring 42 seconds of plasma exposure versus about 155 seconds for the forming gas generated plasma.

FIG. 7 are pictorial views of scanning electron micrographs showing a cross sectional and top down view of a contact hole before and after an oxygen free plasma stripping process according to the process described in Example 2. The contact holes were first patterned using conventional lithographic methods into a DUV photoresist layer which had been coated over a thin layer of organic bottom anti-reflective coating. The substrate was a silicon wafer having deposited or coated thereon a thin nitride layer, a layer of hydrogen silsesquioxanes (HSQ), and a layer of tetraethylorthosilicate (TEOS). A conventional plasma process was employed to etch the contact hole through the patterned resist and into the substrate, as shown in the "before" scanning electron micrographs (SEM) of FIG. 7. The oxygen free plasma stripping process according to Example 2 was utilized and the resulting SEMs after plasma stripping are shown in the "after" SEMs of FIG. 7. No deionized water rinse was used. The "before" and "after" SEMs clearly show the complete removal of photoresist and residues. Moreover, the underlying dielectric layers, TEOS and HSQ, were not deleteriously affected by the oxygen free plasma.

The foregoing description of the preferred embodiments of the invention have been presented for purposes of illustration and description. It is not intended to be exhaustive or to limit the invention to the precise forms disclosed. Obvious modifications or variations are possible considering the above teachings. The embodiments were chosen and described to provide the best illustration of the principles of the invention and its practical applications to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally and equitably entitled.

What is claimed is:

1. A method for determining an endpoint for an oxygen free plasma ashing process wherein said inethod comprises exciting a gas composition containing a nitrogen gas and a selected one of a hydrogen bearing gas, a fluorine bearing gas and a fluorine-hydrogen bearing gas mixture to form an oxygen free plasma, reactng the oxygen free plasma with a substrate having a photoresist and/or residues thereon to produce emitted light signals corresponding to an oxygen free reaction product; sequentially recording over a period of time the light emission intensity signals resulting form the reaction product; and deter said endpoint at a time when the light emission intensity signals of said reaction product are at a threshold level, said level indicating the ashing process is substantially complete.

2. The method according to claim 1 further comprising measuring the light intensity signals at a wavelength of about 387 nm for determining said endpoint.

3. The method according to claim 1 or 2 further comprising measuring secondary light intensity signals at wavelengths of about 358 nm and about 431 nm for determining said endpoint.

4. The method according to claim 1 further comprising using optical emission spectroscopy for measuring said light intensity signals.

5. The method according to claim 4 wherein said optical emission spectroscopy comprises a selected one of a monochromator and a spectrometer.

6. The method according to claim 5 wherein equipment used for said optical emission spectroscopy is a selected one of a spectral filter and light detector combination, a monochromator, a CCD spectrophotometer, a photodetector array and a scanning monochromator.

7. The method according to claim 1 wherein the endpoint is detected when said light emission intensity signals of said reaction are at a threshold intensity value, wherein said threshold intensity value is calculated by experimentation by correlating values of reaction time, light wavelength spectrum and light emission intensity signals, and said value corresponds to a condition wherein the ashing process is substantially complete.

8. The method according to claim 1 wherein said substrate comprises a semiconductor wafer having therein a material having a low k dielectric constant less than about 3.5 and/or exposed copper surfaces.

9. The method according to claim 1 wherein said fluorine bearing gas is selected from the group consisting of $NF_3$, $F_2$, $SF_6$, and $C_xH_yF_z$ wherein x ranges from 1 to 4, y ranges from 0 to 9 and z ranges from 1 to 10.

10. The method according to claim 1 wherein said hydrogen gas mixture comprises a forming gas comprising nitrogen and hydrogen gas wherein said hydrogen gas is in an amount from about 3 percent to about 5 percent by volume of the forming gas.

11. A method for determining an endpoint for an oxygen free plasma asbing process wherein said method comprises exciting a gas composition containing a nitrogen gas and a selected one of a hydrogen bearing gas, a fluorine bearing gas and a fluorine-hydrogen bearing gas mixture to form an oxygen free plasma; reacting the oxygen free plasma with a substrate having photoresist and/or residues thereon to produce volatile reaction products; measuring an emission signal of said products at a wavelength of about 387 nm and determining said endpoint in response to an observed change in the monitored emission signal.

12. The method according to claim 11 further comprising measuring emission signals at wavelengths of about 358 nm and 431 nm wherein said endpoint is determined in response to the observed change in the monitored emission signals.

13. The method according to claim 11 further comprising using optical emission spectroscopy for measuring said emission signals.

14. The method according to claim 13 wherein equipment used for said optical emission spectroscopy is a selected one of a spectral filter and light detector combination, a monochromator, a CCD spectrophotometer, a photodetector array and a scanning monochromator.

15. The method according to claim 13 wherein said optical emission spectroscopy is a selected one of a monochromator and a spectrometer.

16. A method for determining an endpoint of an oxygen free plasma ashing process used for stripping photoresist and/or residues from a substrate, said method comprising the steps of:

generating an oxygen free plasma from a gas composition containing a nitrogen gas and at least one reactive gas;

measuring a first emission signal at a wavelength of about 387 nm;

placing a coated substrate having the photoresist and/or residues thereon into the reaction chamber;

exposing the coated substrate to said plasma;

reacting a substantially electrically neutral species of said oxygen free plasma with said photoresist and/or said residues;

measuring a second emission signal at a wavelength of about 387 nm; and determining said endpoint of the plasma ashing process by comparing said first signal with said second signal wherein said endpoint is detected when said first and second signals are about the same.

17. The method according to claim 16 wherein the first emission signal further comprises wavelengths at about 358 nm and about 431 nm and the second emission signal further comprises wavelengths at about 358 nm and about 431 nm.

18. The method according to claim 16 further comprising subtracting the first signal from the second signal wherein said endpoint is detected when said second signal reaches a steady state having about a zero emission intensity.

19. The method according to claim 16 further comprising placing at least one uncoated substrate into the reaction chamber for measuring the first emission signal.

20. The method according to claim 16 further comprising detecting an endpoint when said second emission signal intensity is at a threshold intensity value, wherein said threshold intensity value is calculated by experimentation by correlating values of reaction time, light wavelength spectrum and light emission intensity signals, and said value corresponds to a condition wherein the ashing process is substantially complete.

21. The method according to claim 16 further comprising using optical emission spectroscopy for measuring said light intensity signals.

22. The method according to claim 21 wherein said optical emission spectroscopy is a monochromator.

23. The method according to claim 16 further comprising step-wise heating said substrate from a range of about 80° C. to about 350° C. during said exposure to said plasma.

24. The method according to claim 16 wherein said substrate comprises a low k dielectric material less than about 3.5 and/or an exposed copper surface.

25. An ashing step for removing photoresist and/or residues from a substrate comprising:

placing the substrate having the photoresist and/or residues thereon into a reaction chamber;

generating an oxygen free plasma from a gas composition containing nitrogen gas and at least one reactive gas;

exposing said photoresist and/or residues to a substantially electrically neutral species of said oxygen free plasma;

reacting said photoresist and/or post etch residues with the neutral species to produce byproducts having emission signals at about 358 nm, 387 nm, and 431 nm;

optically measuring said emission signals of said byproducts; and stopping the ashing step when the emission signals from said reaction byproducts are no longer detectable.

26. The method according to claim 25 wherein optically measuring said emission signals is by optical emission spectroscopy.

27. The method according to claim 26 wherein said optical emission spectroscopy comprises a selected one of a monochromator and a spectrometer.

28. A method for determining an endpoint of an oxygen free plasma ashing process used for stripping photoresist and/or residues from a substrate having low k dielectric layers having a dielectric constant less than about 3.5, said method comprising the steps of:

placing the substrate having the photoresist and/or residues thereon into a reaction chamber;

generating an oxygen free plasma from a gas composition including nitrogen and a reactive gas;

reacting a substantially electrically neutral reactive species of said oxygen free plasma with said photoresist and/or said residues to produce an emission light;

recording an emission intensity spectrum of said emitted light during said reaction wherein said emission intensity spectrum includes a wavelength of about 387 nm; and determining said endpoint of the plasma stripping process from said emission intensity spectrum wherein said endpoint is detected in response to an observable change at about 387 nm.

29. The method according to claim 28 further comprising using optical emission spectroscopy for measuring said light intensity signals.

30. The method according to claim 29 wherein said optical emission spectroscopy comprises a spectrometer.

31. The method according to claim 29 wherein said emission intensity spectrum further includes wavelengths of about 358 nm and about 431 nm.

32. A method for determining an endpoint for an oxygen free plasma ashing process wherein said method comprises exciting a gas composition containing nitrogen gas and a selected one of a hydrogen bearing gas, a fluorine bearing gas and a fluorine-hydrogen bearing gas mixture to form an oxygen free plasma; reacting the oxygen free plasma with a substrate having photoresist and/or residues thereon to produce volatile reaction products, measuring a selected one of an emission signal of said products at wavelengths of about 358 nm, about 387 nm and about 431 nm, and determining said endpoint in response to an observed change in the monitored emission signal.

* * * * *